United States Patent
Wood et al.

(10) Patent No.: US 10,863,969 B2
(45) Date of Patent: Dec. 15, 2020

(54) SYSTEMS WITH SONIC VISUALIZATION CAPABILITY AND RELATED METHODS

(71) Applicant: Boston Scientific Scimed, Inc., Maple Grove, MN (US)

(72) Inventors: Mark D. Wood, Sterling, MA (US); Paul D. Aquilino, Walpole, MA (US); Ryan Hartman, Kingston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 625 days.

(21) Appl. No.: 15/435,772

(22) Filed: Feb. 17, 2017

(65) Prior Publication Data
US 2017/0238903 A1   Aug. 24, 2017

Related U.S. Application Data

(60) Provisional application No. 62/296,656, filed on Feb. 18, 2016.

(51) Int. Cl.
*A61B 8/00* (2006.01)
*A61B 8/12* (2006.01)
(Continued)

(52) U.S. Cl.
CPC .......... *A61B 8/4494* (2013.01); *A61B 1/018* (2013.01); *A61B 8/12* (2013.01); *A61B 8/445* (2013.01);
(Continued)

(58) Field of Classification Search
CPC ......... A61B 8/12; A61B 8/445; A61B 8/4494; A61B 1/018; A61B 17/3478; A61B 8/4483; B06B 1/0292; A61M 25/0067
See application file for complete search history.

(56) References Cited

U.S. PATENT DOCUMENTS 4,398,116 A   8/1983 Lewis
5,186,177 A   2/1993 O'Donnell et al.
(Continued)

FOREIGN PATENT DOCUMENTS

EP   0 671 221 A2   9/1995
EP   2 596 753 A1   5/2013
(Continued)

OTHER PUBLICATIONS

Butrus T. Khuri-Yakub and Ömer Oralkan, 2011, J Micromech Microeng, 21(5): 054004-054014 (Year: 2011).*
(Continued)

*Primary Examiner* — Angela M Hoffa
(74) *Attorney, Agent, or Firm* — Bookoff McAndrews, PLLC (57) ABSTRACT

According to aspects of the present disclosure, a system for visualizing a target area may include an elongate shaft. The elongate shaft may include a distal portion, a lumen that extends longitudinally through the distal portion, and an opening at the distal end of the distal portion. The opening may be in communication with the lumen. The system also may include a visualization assembly housed within the distal portion of the elongate shaft. The visualization assembly may include a transducer array having a field of view in which the transducer array transceives sound waves. The field of view of the transducer array may cover at least part of the distal portion of the elongate shaft and the target area to facilitate visualization of the part of the distal portion of the elongate shaft and the target area.

15 Claims, 4 Drawing Sheets

(51) Int. Cl.
*A61M 25/00* (2006.01)
*A61B 1/018* (2006.01)
*A61B 17/34* (2006.01)
*B06B 1/02* (2006.01)

(52) U.S. Cl.
CPC ........ *A61B 8/4483* (2013.01); *A61B 17/3478* (2013.01); *A61M 25/0067* (2013.01); *B06B 1/0292* (2013.01)

(56) References Cited

U.S. PATENT DOCUMENTS

| | | | | |
|---|---|---|---|---|
| 5,938,671 | A * | 8/1999 | Katoh | A61B 17/3207 606/159 |
| 6,068,638 | A * | 5/2000 | Makower | A61B 1/3137 606/159 |
| 6,157,852 | A * | 12/2000 | Selmon | A61B 8/12 128/898 |
| 6,241,667 | B1 * | 6/2001 | Vetter | A61B 8/12 600/407 |
| 6,306,097 | B1 * | 10/2001 | Park | A61B 1/00154 600/466 |
| 6,457,365 | B1 * | 10/2002 | Stephens | A61B 8/12 600/447 |
| 6,464,710 | B1 | 10/2002 | Foster | |
| 8,803,259 | B2 | 8/2014 | Chen | |
| 8,936,553 | B2 * | 1/2015 | Stigall | A61B 6/504 600/439 |
| 2005/0203416 | A1 | 9/2005 | Angelsen et al. | |
| 2006/0036234 | A1 | 2/2006 | Durgin et al. | |
| 2007/0016054 | A1 * | 1/2007 | Cao | A61B 8/06 600/459 |
| 2007/0167804 | A1 * | 7/2007 | Park | A61B 5/0066 600/459 |
| 2009/0030312 | A1 * | 1/2009 | Hadjicostis | A61B 8/12 600/439 |
| 2010/0251823 | A1 | 10/2010 | Adachi et al. | |
| 2012/0123271 | A1 * | 5/2012 | Cai | A61B 8/06 600/454 |
| 2013/0150716 | A1 * | 6/2013 | Stigall | A61B 6/504 600/439 |
| 2013/0172682 | A1 | 7/2013 | Ransden et al. | |
| 2013/0172855 | A1 | 7/2013 | Wood et al. | |
| 2014/0005521 | A1 | 1/2014 | Kohler et al. | |
| 2014/0012125 | A1 | 1/2014 | Chen | |
| 2014/0066706 | A1 | 3/2014 | McWeeney et al. | |
| 2014/0257102 | A1 | 9/2014 | Hossack | |
| 2015/0164470 | A1 | 6/2015 | Shiotani et al. | |
| 2015/0289750 | A1 | 10/2015 | Stigall et al. | |
| 2015/0342530 | A1 | 12/2015 | Dekker et al. | |

FOREIGN PATENT DOCUMENTS

| | | |
|---|---|---|
| JP | H09-28710 A | 2/1997 |
| JP | 2004-350701 A | 12/2004 |
| JP | 2013-544150 A | 12/2013 |

OTHER PUBLICATIONS

International Search Report and Written Opinion for Int'l Application No. PCT/US2017/018317, dated May 10, 2017 (17 pages).
Nikoozadeh et al., "Forward-Looking Intracardiac Imaging Catheters Using Fully Integrated CMUT Arrays" (4 pages).
Gurun et al., "Single-Chip CMUT-on-CMOS Front-End System for Real-Time Volumetric IVUS and ICE Imaging," IEEE Transactions on Ultrasonics, Ferroelectrics, and Frequency Control, vol. 61, No. 2, Feb. 2014, pp. 239-250 (12 pages).
Taranovich, "Flexible medical sensors aid diagnoses," Sep. 20, 2013 (4 pages).
Oralkan et al., "Capacitive Micromachined Ultrasonic Transducers: Next-Generation Arrays for Acoustic Imaging?" IEEE Transactions on Ultrasonics, Ferroelectrics, and Frequency Control, vol. 49, No. 11, Nov. 11, 2002, pp. 1596-1610 (15 pages).
Boston Scientific Brochure, "Hemostasis Solutions," (6 pages).
Boston Scientific Brochure, "NovaGold™ High Performance Guidewire," (7 pages).
Boston Scientific Brochure, "SpyGlass™ DS Direct Visualization System," (11 pages).
Boston Scientific Brochure, "Autotome™ RX Cannulating Sphincterotome," (6 pages).

* cited by examiner

SYSTEMS WITH SONIC VISUALIZATION CAPABILITY AND RELATED METHODS

CROSS-REFERENCE TO RELATED APPLICATIONS

This application claims the benefits of priority from U.S. Provisional Application No. 62/296,656, filed on Feb. 18, 2016, the entirety of which is incorporated herein by reference.

TECHNICAL FIELD

Various aspects of the present disclosure relate generally to apparatuses with visualization capabilities and related methods. More specifically, the present disclosure relates to apparatuses with sonic visualization capabilities and related methods.

BACKGROUND

During certain procedures in which a user examines and/or treats a subject, the user may insert a system into the subject's body. The user may position the system within the subject's body to view and/or perform a procedure on a target area. The target area may include, for example, an interior of a hollow organ, a cavity, or a lumen in the subject's body. Conventional visualization modalities may be used to help the user guide the system to the target area, and to position the system at the target area. Such visualization modalities may include, for example, optical visualization or fluoroscopy. Optical visualization may be hindered in some instances by objects or material obscuring line of sight. Fluoroscopy exposes the user and/or subject to ionizing radiation. Enhancing a system's visualization capabilities by replacing or supplementing conventional visualization modalities may lead to improved outcomes.

SUMMARY

Aspects of the present disclosure relate to, among other things, systems with sonic visualization capabilities and related methods. Each of the aspects disclosed herein may include one or more of the features described in connection with any of the other disclosed aspects.

In one aspect of the present disclosure, a system for visualizing a target area may include an elongate shaft. The elongate shaft may include a distal portion, a lumen that extends longitudinally through the distal portion, and an opening at the distal end of the distal portion. The opening may be in communication with the lumen. The system also may include a visualization assembly housed within the distal portion of the elongate shaft. The visualization assembly may include a transducer array having a field of view in which the transducer array transceives sound waves. The field of view of the transducer array may cover at least part of the distal portion of the elongate shaft and the target area to facilitate sonic visualization of the part of the distal portion of the elongate shaft and the target area.

Aspects of the system may include one or more of the features below. The transducer array may surround at least a portion of the lumen. The transducer array may include at least one ultrasonic transducer. The ultrasonic transducer may include a capacitive micromachined ultrasonic transducer. The sonic visualization assembly may have a distalmost end, and the transducer array may include at least one transducer at the distalmost end. The opening may be a first opening, and the at least one transducer may include an annular plate having a plurality of transducers thereon, and a second opening that may extend through the annular plate. The opening may be a first opening, the elongate shaft may include a second opening at the distal end of the distal portion, and the system may further include an optical visualization assembly received in the second opening. The elongate shaft may have a distalmost end, and the transducer array may include at least one transducer configured to transmit sound waves toward a region distal to the distalmost end, and to receive sound waves from the region. The transducer array may include at least one transducer on a side of the visualization assembly. The at least one transducer may include a plate having a plurality of transducers thereon. The at least one transducer may include a plurality of plates, each of the plates may have a plurality of transducers thereon, and the plates may be arranged in a ring formation. The transducer array may include at least one transducer configured to transmit sound waves toward a region lateral to the distal portion of the elongate shaft, and receive sound waves from the region. The system may further include a control member coupled to the distal portion of the elongate shaft to exert a deflecting force on the distal portion, such that the visualization assembly deflects with the distal portion.

In another aspect of the present disclosure, a system for visualizing a target area may include an introducer. The introducer may include a first elongate shaft, and a plurality of lumens in the first elongate shaft. The plurality of lumens may include a first lumen that extends longitudinally through the first elongate shaft. The system also may include a visualization assembly slidably received by the introducer. The visualization assembly may include a second elongate shaft, and a transducer array at a distal portion of the second elongate shaft. The transducer array may be configured to transceive sound waves for visualization of the target area, and to slide proximally and/or distally relative to the first elongate shaft within the first lumen.

Aspects of the system may include one or more of the features below. The introducer may further include an optical visualization assembly, and the optical visualization assembly may include an imaging device at a distal end of the introducer. The first elongate shaft may have a distal end, and the transducer array may be extendable distally beyond the distal end of the first elongate shaft. The transducer array may include a capacitive micromachined ultrasonic transducer array.

In another aspect of the present disclosure, a system for visualizing a target area may include an elongate shaft. The elongate shaft may include a distal end, and an opening at the distal end. The system also may include an optical visualization assembly within the opening of the elongate shaft, wherein the optical visualization assembly may include an imaging device configured to generate an image of the target area. The system also may include a sonic visualization assembly at the distal end of the elongate shaft, wherein the sonic visualization assembly may include a transducer array configured to transmit and receive sound waves for visualizing the target area.

Aspects of the system also may include one or more of the features below. The opening may be at the distal end may be a first opening, the elongate shaft may include a second opening at the distal end of the shaft beside the first opening, and at least a portion of the sonic visualization assembly may be within the second opening. The first opening and the second opening may be in a distalmost surface of the distal end of the elongate shaft.

It may be understood that both the foregoing general description and the following detailed description are exemplary and explanatory only and are not restrictive of the features claimed.

As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn generally to apparatuses with visualization capabilities and related methods, and more specifically, to those with sonic visualization capabilities and their related methods. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing an instrument into a subject. By contrast, the term "proximal" refers to a portion closest to the user when placing the instrument into the subject. Though the following description refers to an "endoscope system," a "cutting system," and an "injection system," the principles/aspects described herein may be used with any suitable systems, even if systems fall outside these enumerated categories.

Figure 1:
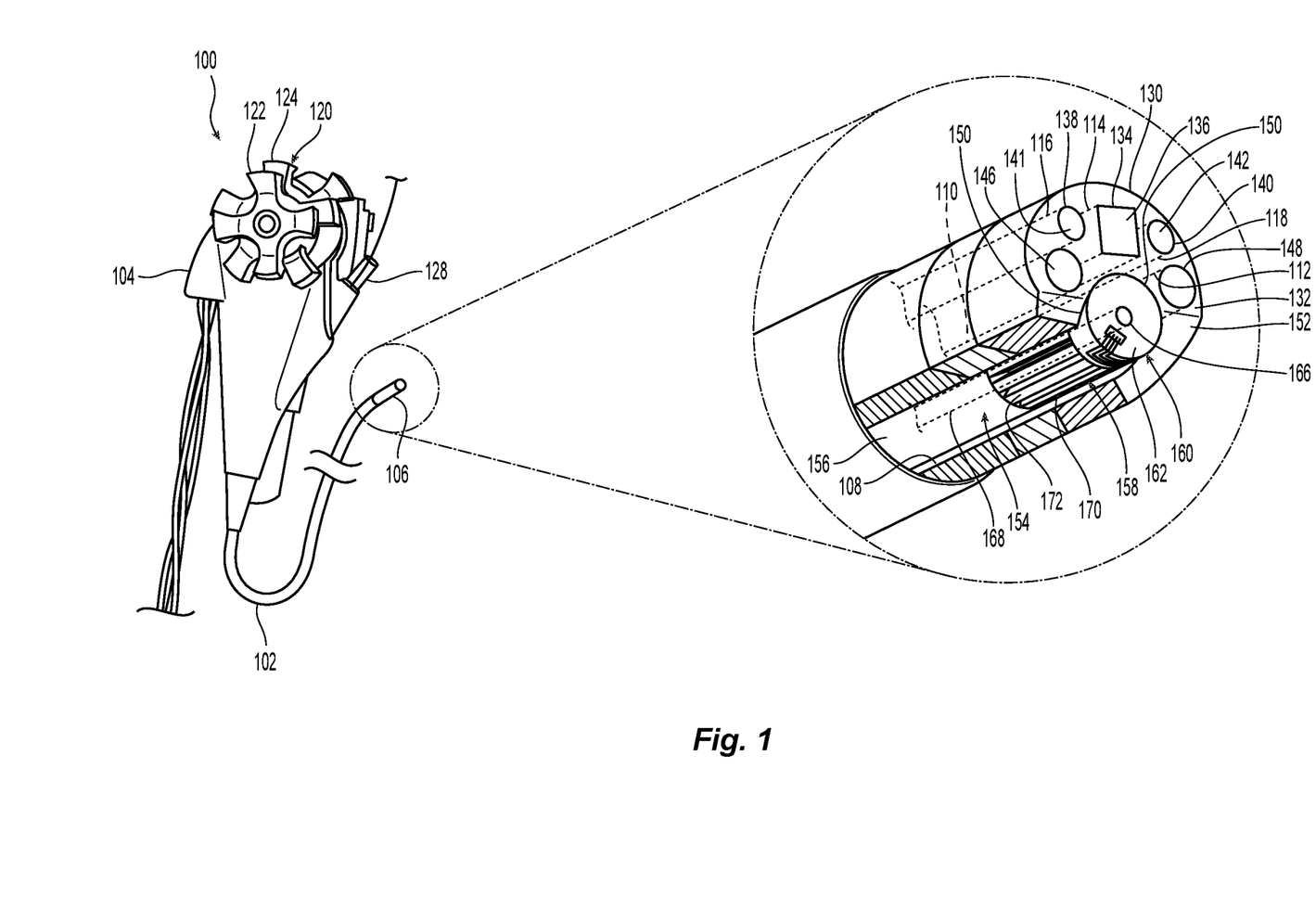
FIG. 1 is a perspective view of an exemplary endoscope system, including a close-up partial cross-sectional view of an end portion, in accordance with aspects of the present disclosure.

FIG. 1 shows an exemplary endoscope system 100 in accordance with aspects of the present disclosure. FIG. 1 includes a close-up view of an end portion of endoscope system 100. The close-up view is a partial cross-sectional view, cut away to show details of the internals of endoscope system 100.

Endoscope system 100 may include a shaft 102 and a handle 104. Shaft 102 may include an elongated flexible body that extends from a distal end of handle 104. In one example, shaft 102 may include an articulation or bending section 106 disposed at a distal region thereof. Shaft 102 may be constructed of polyether block amides (e.g., Pebax®), polyurethane, polytetrafluoroethylene (PTFE), polyethylene, fluorinated ethylene propylene (FEP), thermoplastic elastomers, nylon, and/or any other suitable material or combination of materials. While shaft 102 generally may be cylindrical, the close-up view in FIG. 1 includes a partial cross-sectional view of shaft 102, with a lower portion of shaft 102 cut away in the drawing to show aspects inside of shaft 102.

Shaft 102 may have one or more lumens extending therethrough. For example, shaft 102 may have a working lumen 108 that allows for the passage of various treatment or diagnostic instruments through shaft 102 including, for example, guidewires, kidney stone retrieval baskets, laser emitters, biopsy forceps, needles, and/or any other suitable instruments. Shaft 102 may have one or more fluid lumens 110, 112 for facilitating the insertion and extraction of fluid and/or gas into and out of the subject's body. Fluid lumen 110 may, for example, be used as an irrigation lumen, insufflation lumen, aspiration lumen, and/or suction lumen. Fluid lumen 112 may be similar to fluid lumen 110. Fluid lumen 112 may be disposed along a side of shaft 102 opposite that of fluid lumen 110. It is contemplated that fluid lumens 110, 112 also may receive treatment or diagnostic instruments. Shaft 102 may have an optical visualization lumen 114 for receiving an optical visualization assembly 136. Shaft 102 may have one or more illumination lumens 116, 118. Illumination lumens 116 and 118 may be similar, but may be disposed along opposing sides of shaft 102.

Shaft 102 also may include one or more steering or control members (e.g., wires) (not shown). The one or more steering wires may extend through steering wire lumens within shaft 102. In one example, shaft 102 may include a pair of steering wires for controlling articulation of shaft 102 along a first plane (e.g., in the up and down directions). In another example, shaft 102 may include two pairs of steering wires, a first pair for controlling articulation of shaft 102 along the first plane, and a second pair for controlling articulation of shaft 102 along a second plane transverse to the first plane (e.g., in the left and right directions). Distal ends of the steering wires may be coupled to the distal region of shaft 102 by, for example, adhesive bonding, heat bonding, crimping, laser welding, resistance welding, soldering, and/or any other suitable form of attachment, such that pulling forces exerted on the steering wires may be applied to the distal region of shaft 102 (and particularly articulation section 106) where the steering wires and shaft 102 are coupled.

A proximal end of shaft 102 may be coupled to the distal end of handle 104. Handle 104 may include an articulation control assembly 120 for controlling articulation of articulation section 106 of shaft 102. In one example, articulation control assembly 120 may include one or more control knobs 122, 124 that may be connected to proximal portions of the steering wires, for exerting pulling forces on the steering wires. Handle 104 may include one or more ports for providing access to one or more of the lumens of shaft 102 from a position exterior to handle 104. For example, a port 128 may be in communication with working lumen 108.

Shaft 102 may include an end cap 130 at its distal end. In one example, end cap 130 may be cylindrical. A distal face 132 of end cap 130 may have one or more openings. For example, distal face 132 may have an optical visualization opening 134 in communication with optical visualization lumen 114 for receiving a distal end of optical visualization assembly 136. Distal face 132 may have one or more illumination openings 138, 140 in communication with one or more illumination lumens 116, 118 for receiving distal ends of one or more illumination assemblies 141, 142. Distal face 132 may have one or more fluid openings 146, 148 in communication with one or more fluid lumens 110, 112 for irrigation, insufflation, aspiration, and/or suction. Distal face 132 may have a working opening 150 in communication with working lumen 108 for receiving treatment or diagnostic instruments. End cap 130 may have a tapering region 152 for, among other things, facilitating the insertion of end cap 130 into small openings in the subject's body, and exposing portions of instruments in working opening 150 that would otherwise be covered if distal face 132 was entirely planar. One portion of working opening 150 may be on tapering region 152, and another portion of working opening 150 may be on distal face 132.

Endoscope system 100 may be provided with one or more visualization capabilities. For example, endoscope system 100 may be used to introduce a sonic visualization assembly 154 to the target area. Sonic visualization assembly 154 may include an instrument inserted into shaft 102 and guided to end cap 130 via working lumen 108. Sonic visualization assembly 154 may include a shaft 156. Shaft 156 may be flexible so as to bend with shaft 102. A transducer or transducer array 158 may be positioned on or in a distal portion of shaft 156. One or more of the transducers may include, for example, a capacitive micromachined ultrasonic transducer (CMUT). The CMUT may be constructed using silicon machined with micromachining techniques. In one example, a recess or cavity may be formed in a silicon substrate. A membrane may be suspended above the cavity. A metallized layer may be provided on the membrane, and may serve as a top electrode. The silicon substrate may serve as a bottom electrode.

When an electrical signal is applied across the electrodes, the vibrating membrane may produce ultrasonic waves in materials in the subject's body. The ultrasonic waves may echo off of the materials. Different materials may reflect varying degrees of the ultrasonic waves. The reflected ultrasonic waves may be directed back toward the CMUT. When those reflected ultrasonic waves are applied on the membrane, the CMUT may generate an electrical signal as the capacitance of the CMUT is varied. The electrical signal may be indicative of one or more characteristics of the materials that reflected the ultrasonic waves. The electrical signal may be processed into an image of the materials.

Because the CMUT may be micromachined, it may be compact. Its compactness lends it to arrangement in one-dimensional, two-dimensional, and three-dimensional arrays. Such arrangements allow large numbers of CMUTs to be utilized on small instruments or devices. The large numbers of CMUTs provide a greater bandwidth compared to conventional transducer technologies.

Transducer array 158 may include a forward-looking or front-end CMUT array 160. A distal surface of front-end CMUT array 160, which may be used to transmit and receive ultrasonic waves, may face the distal direction, and/or may extend in a plane substantially perpendicular to a central longitudinal axis of shaft 156 and/or shaft 102. The field of view of front-end CMUT array 160 may cover regions that receive sound waves transmitted by front-end CMUT array 160, and/or regions from which front-end CMUT array 160 receives reflections of the transmitted sound waves. For example, the field of view of front-end CMUT array 160 may cover a region immediately distal to front-end CMUT array 160, and some areas adjacent to the region.

Front-end CMUT array 160 may be in the form of a plate 162. Plate 162 may be annular, with an opening 166 therein. Opening 166 may be in communication with a lumen 168 extending through shaft 156. Opening 166 and lumen 168 may be configured to receive treatment or diagnostic instruments, such as guidewires, kidney stone retrieval baskets, laser emitters, biopsy forceps, needles, and/or any other suitable instruments. Thus, the instruments may be positioned within working lumen 108 and/or working opening 150 at the same time as sonic visualization assembly 154, without sonic visualization assembly 154 blocking the instruments or otherwise preventing their use. It is also contemplated that front-end CMUT array 160 may be operated simultaneously with use of the instruments, allowing the user to use images obtained via front-end CMUT array 160 to help guide the instruments as they are extended distally out of opening 166 and into the target area to perform diagnoses or procedures therein. Alternatively, opening 166 and/or lumen 168 may be omitted, such that sonic visualization assembly 154 may block working lumen 108 and/or working opening 150, allowing a larger array of CMUTs to be used for visualization purposes.

In addition to front-end CMUT array 160, or as an alternative to front-end CMUT array 160, sonic visualization assembly 154 may include a side-looking or lateral-facing CMUT array 170. Lateral-facing CMUT array 170 may include tiles 172 in the form of polygonal plates, with transmitting and receiving surfaces of tiles 172 facing radially outwardly relative to the central longitudinal axis of shaft 156. Tiles 172 may be arranged to form a ring about shaft 156. Tiles 172 may surround lumen 168 of shaft 156.

The field of view of lateral-facing CMUT array 170 may cover regions that receive sound waves transmitted by lateral-facing CMUT array 170, and/or regions from which lateral-facing CMUT array 170 receives reflections of the transmitted sound waves. For example, each of tiles 172 may have a field of view covering a region immediately lateral to it, and some areas adjacent to the region. Tiles 172 may be spaced around shaft 156 such that their fields of view may overlap. The overlap may provide lateral-facing CMUT array 170 with the ability to visualize a 360 degree area surrounding lateral-facing CMUT array 170. While a plurality of tiles 172 are shown in FIG. 1, it should be understood that fewer tiles 172 may be used, or even a single tile 172 only may be used for visualizing a more focused area.

Front-end CMUT array 160 and lateral-facing CMUT array 170 may operate simultaneously, with front-end CMUT array 160 providing sonic visualization of a region of the target area distal to front-end CMUT array 160, and lateral-facing CMUT array 170 providing sonic visualization of a region or regions of the target area beside or surrounding lateral-facing CMUT array 170. Alternatively, only one of front-end CMUT array 160 and lateral-facing CMUT array 170 may be operated at one time to, for example, conserve power. Front-end CMUT array 160 and/or lateral-facing CMUT array 170 may be switched on depending on the region of the target area the user would like to visualize.

A distal end of sonic visualization assembly 154 may be inserted into working port 128 by the user. The user may continue to insert sonic visualization assembly 154 into working lumen 108 of shaft 102, bringing shaft 156 into working lumen 108, and pushing the distal end of sonic visualization assembly 154 toward end cap 130. The user may position the distal end of sonic visualization assembly 154 relative to end cap 130 such that the distal transmitting/receiving surface of front-end CMUT array 160 may be within a portion of working lumen 108, within working opening 150, flush with a portion of distal face 132, distal to distal face 132, or to any position therebetween. In instances where a portion of shaft 102 is within the field of view of front-end CMUT array 160 (e.g., when the distal surface of front-end CMUT array 160 is within working lumen 108 or working opening 150), front-end CMUT array 160 may facilitate visualization of the portion of shaft 102 and the target area. This may provide the user with the ability to orient the portion of shaft 102 relative to, for example, an anatomical landmark.

Additionally or alternatively, the user may position a portion or all of lateral-facing CMUT array 170 relative to end cap such that it is within working lumen 108, within opening 150, distal to distal face 132, or to any position therebetween. front-end CMUT array 160 and/or lateral-facing CMUT array 170 may be capable of transmitting and receiving ultrasonic waves through the material used to construct endoscope system 100. It is also contemplated that, in one example, at least a lower portion of lateral-facing CMUT array 170 may be exposed, even though an upper portion of lateral-facing CMUT array 170 may not be, due to taper 152. As such, even when front-end CMUT array 160 is within working opening 150 or flush with distal face 132, one or more portions of lateral-facing CMUT array 170 may transmit/receive sound waves without being obstructed by end cap 130. In instances where a portion of shaft 102 is within the field of view of lateral-facing CMUT array 170 (e.g., when at least a portion of a radially-outward facing surface of lateral-facing CMUT array 170 is within working lumen 108 or working opening 150), lateral-facing CMUT array 160 may facilitate visualization of the portion of shaft 102 and the target area. This may provide the user with the ability to orient the portion of shaft 102 relative to, for example, an anatomical landmark.

The user may withdraw sonic visualization assembly 154 from working opening 150, working lumen 108, and/or port 128, to clear at least a portion of working opening 150, working lumen 108, and/or working port 128 for receipt of another diagnostic or treatment instrument. The other diagnostic or treatment instrument may, for example, be extended distally out of working opening 150 and into the target area. Examples of other diagnostic or treatment instruments may include, for example, cutting systems and injection systems similar to those described below. Alternatively, the user may leave sonic visualization assembly 154 in place in working opening 150, working lumen 108, and/or working port 128, and insert the other diagnostic or treatment instrument into and through lumen 168 and toward the target area.

Alternatively, sonic visualization assembly 154 may be fixed in and/or to endoscope system 100. In one example, the outer surface of sonic visualization assembly 154 may be attached to one or more surfaces of endoscope system 100 defining port 128, working lumen 108, and/or working opening 150. In another example, front-end CMUT array 160 and/or lateral-facing CMUT array 170 may be present without shaft 156, for example integrated directly into shaft 102 and fixed within shaft 102. Front-end CMUT array 160 may be attached to one or more surfaces of end cap 130 defining working opening 150, with at least a portion of front-end CMUT array 160 extending within working opening 150. Lateral-facing CMUT array 170 may be attached to one or more surfaces of end cap 130 and/or shaft 102 that define working opening 150 and working lumen 108, respectively. At least a portion of lateral-facing CMUT array 170 may extend within working opening 150 and/or working lumen 108. Alternatively, at least a portion of lateral-facing CMUT array 170 may be embedded in, or otherwise contained in, the material(s) surrounding working opening 150 and/or working lumen 108, such that lateral-facing CMUT array 170 surrounds working opening 150 and/or working lumen 108 without extending into working opening 150 and/or working lumen 108. In yet another example, front-end CMUT array 160 may be attached at distal face 132 and may circumscribe working opening 150, illumination opening 138, illumination opening 140, fluid opening 146, fluid opening 148, or optical visualization opening 134. In yet another example, front-end CMUT array 160 may be attached at distal face 132 and may circumscribe a plurality of the end cap openings. Sonic visualization assembly 154, front-end CMUT array 160, and/or lateral-facing CMUT array 170 may be attached to endoscope system 100 by adhesive bonding, heat bonding, crimping, laser welding, resistance welding, soldering, and/or any other suitable form of attachment.

Sonic visualization assembly 154 may be used to provide 2-D and 3-D visualization of the target area. For example, sonic visualization assembly 154 may provide 2-D visualization by transmitting and receiving ultrasonic waves while remaining in a fixed position at the target area. Additionally or alternatively, sonic visualization assembly 154 may provide 3-D visualization by transmitting and receiving ultrasonic waves in multiple positions at the target area. At each of those positions, sonic visualization assembly 154 may produce a 2-D visualization. Those 2-D visualizations may be processed and combined to form a 3-D visualization. The 3-D visualization may be facilitated by controlled/predetermined movement(s) of sonic visualization assembly 154 relative to endoscope system 100 and the target area, and/or by controlled/predetermined movement(s) of endoscope system 100 and sonic visualization assembly 154 relative to the target area. The controlled/predetermined movement(s) may be imparted using, for example, a sled assembly configured to move sonic visualization assembly 154 and/or endoscope system 100 in longitudinal directions at predetermined rates and/or over predetermined distances. 2-D visualizations may be taken during the controlled/predetermined movement(s), and combined to form the 3-D visualization.

Front-end CMUT array 160 and/or lateral-facing CMUT array 170 may be part of a larger electronic circuit including, for example, one or more printed circuit boards (PCBs) supporting front-end CMUT array 160 and/or lateral-facing CMUT array 170 (where the PCBs may be flexible to facilitate arrangement of front-end CMUT array 160 and/or lateral-facing CMUT array 170 on sonic visualization assembly 154); integrated circuits (ICs) on the PCBs; and conductive pads, wires, and/or traces operatively coupling these electronic components. Electrical power for running the electronic components, and electrical signals for conveying instructions and/or information, may be delivered to and/or received from the electronic components. This description of the electronic circuit is not exhaustive, and it should be understood that additional electronic components and circuit features may be present.

Endoscope system 100 also may include optical visualization assembly 136 for visualization. Optical visualization assembly 136 may include, for example, an image sensor assembly within optical visualization opening 134 of end cap 130. The image sensor assembly may include, for example, a charge coupled device (CCD), complementary metal oxide semiconductor (CMOS), or any other suitable image sensor (not shown), for capturing images at and around distal face 132 of end cap 130 in a digital format. The image sensor assembly also may include one or more glass or polymeric lenses for focusing light onto the image sensor. Image data and control signals may be transmitted along the length of shaft 102 via one or more wires or cables, for processing and/or displaying to the user.

In one example, optical visualization assembly 136 may be operated simultaneously with front-end CMUT array 160 and/or lateral-facing CMUT array 170. For example, optical visualization assembly 136 and front-end CMUT array 160 may operate simultaneously to provide optical and sonic visualization of a region of the target area distal to end cap 130 and front-end CMUT array 160. The visual information provided by optical visualization assembly 136 and front-end CMUT array 160 may be different, and there may be instances where optical visualization assembly 136 may provide a better visual of the region of the target area than front-end CMUT array 160, and vice-versa. As another example, optical visualization assembly 136 and lateral-facing CMUT array 170 may operate simultaneously to provide optical visualization of a region of the target area distal to end cap 130, and sonic visualization of a region or regions of the target area beside or surrounding lateral-facing CMUT array 170, giving the user a greater field of view. Alternatively, optical visualization assembly 136 and front-end CMUT array 160 and/or lateral-facing CMUT array 170 may be operated at separate times.

Due to the proximity of working opening 150 and optical visualization opening 134, the fields of view of optical visualization assembly 136 and front-end CMUT array 160 may overlap. This allows front-end CMUT array 160 in working opening 150, and optical visualization assembly 136 in optical visualization opening 134, to provide information about similar regions of the target area. That way, aspects of the regions of the target area that may not be evident using optical visualization may be more visible by sonic visualization, and vice-versa, thus providing the user with a greater amount of information about the target area. The overlap may be facilitated by aligning front-end CMUT array 160 and optical visualization assembly 136 along a centerline across distal face 132. Front-end CMUT array 160 and/or optical visualization assembly 136 may be symmetrical about the centerline. The overlap also may be facilitated by ensuring that none of illumination openings 138, 140 and fluid openings 146, 148 separate front-end CMUT array 160 from optical visualization assembly 136. In another example, front-end CMUT array 160 may not lie in working opening 150, but rather, may circumscribe optical visualization assembly 136, to create the overlapping fields of view while keeping working opening 150 free of obstruction.

Front-end CMUT array 160 and/or lateral-facing CMUT array 170 may be in electronic communication with a system controller (not shown). The system controller may include any suitable computing or processing device(s). The system controller may run one or more modules or algorithms for controlling operation of front-end CMUT array 160 and/or lateral-facing CMUT array 170 by, for example, sending electronic signals to front-end CMUT array 160 and/or lateral-facing CMUT array 170 to cause ultrasonic waves to be emitted, and receiving electronic signals from front-end CMUT array 160 and/or lateral-facing CMUT array 170 indicative of received ultrasonic waves (e.g., echoes). The system controller also may run one or more modules or algorithms for processing the electronic signals to create visuals from the electronic signals for viewing by the user. The system controller may run similar modules or algorithms for optical visualization via optical visualization assembly 136. The system controller may include one or more pieces of equipment separate from endoscope system 100 and/or sonic visualization assembly 154, and/or may include components contained within endoscope system 100 and/or sonic visualization assembly 154.

The system controller also may control operation of auxiliary systems (not shown) associated with endoscope system 100, such as a fluid or suction source and/or an illumination source. The fluid or suction source may deliver fluid into fluid lumens 110, 112, and/or create a suction force in fluid lumens 110, 112. The illumination source may include, for example, a light-emitting diode (LED) that may deliver illumination light to an optical fiber, or bundle of optical fibers, extending through illumination lumens 116, 118, for emission out of illumination openings 138, 140 of end cap 130. The system controller also may control the supply of electrical power to one or more of the above-described electronic components.

Figure 2:
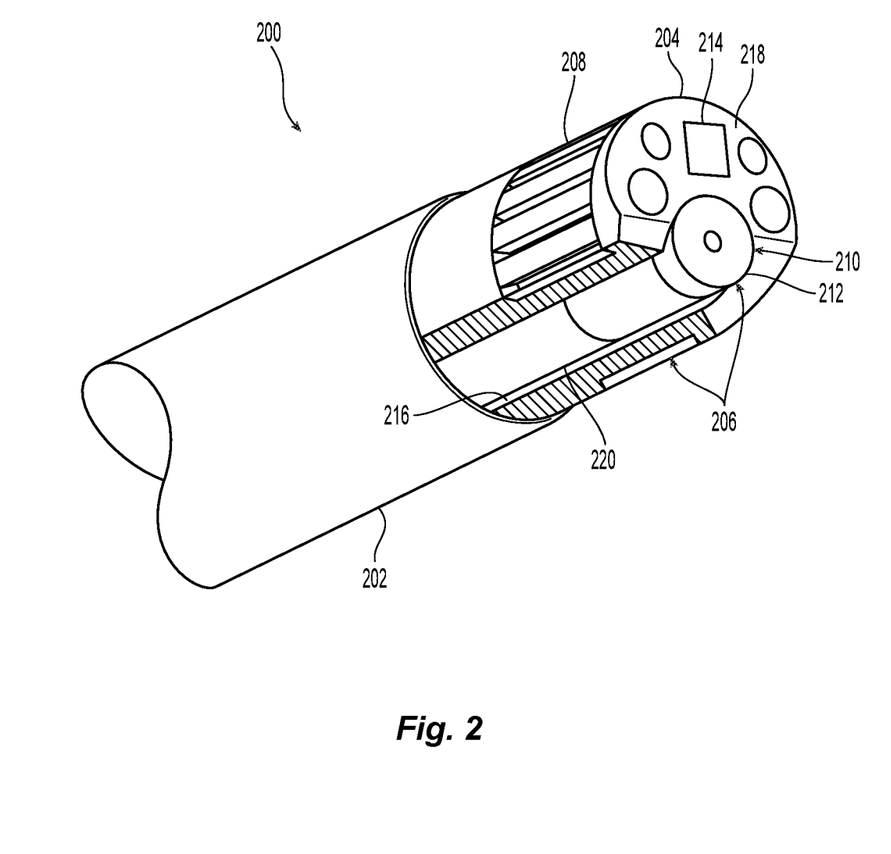
FIG. 2 is a perspective close-up partial cross-sectional view of an end portion of another exemplary endoscope system, in accordance with aspects of the present disclosure.

FIG. 2 shows another exemplary endoscope system 200 in accordance with aspects of the present disclosure. FIG. 2 is a partial cross-sectional view, cut away to show details of the internals of endoscope system 200.

Endoscope system 200 may include a shaft 202 with an end cap 204 similar to shaft 102 and end cap 130. A sonic visualization assembly 206 may be introduced to the target area via shaft 202. A difference between endoscope system 200 and endoscope system 100 is that with endoscope system 200, a side-looking or lateral-facing CMUT array 208 may be provided on or in end cap 204 and/or another portion of shaft 202, rather than on a shaft 220 of sonic visualization assembly 206. That is, lateral-facing CMUT array 208 may be arranged in a ring on or within a periphery of end cap 204 and/or shaft 202. A forward-looking or front-end CMUT array 210 may be arranged on a distal end of shaft 220. Alternatively, lateral-facing CMUT array 208 may be arranged in a ring on sonic visualization assembly 206, while forward-looking or front-end CMUT array 210 may be arranged on a distal face 218 of end cap 204 around, for example, a working opening 212 or an optical visualization opening 214. Front-end CMUT array 210 may be similar to front-end CMUT array 160. 2-D and 3-D visualization may be provided by sonic visualization assembly 206 in a manner similar to sonic visualization assembly 154.

Figure 3:
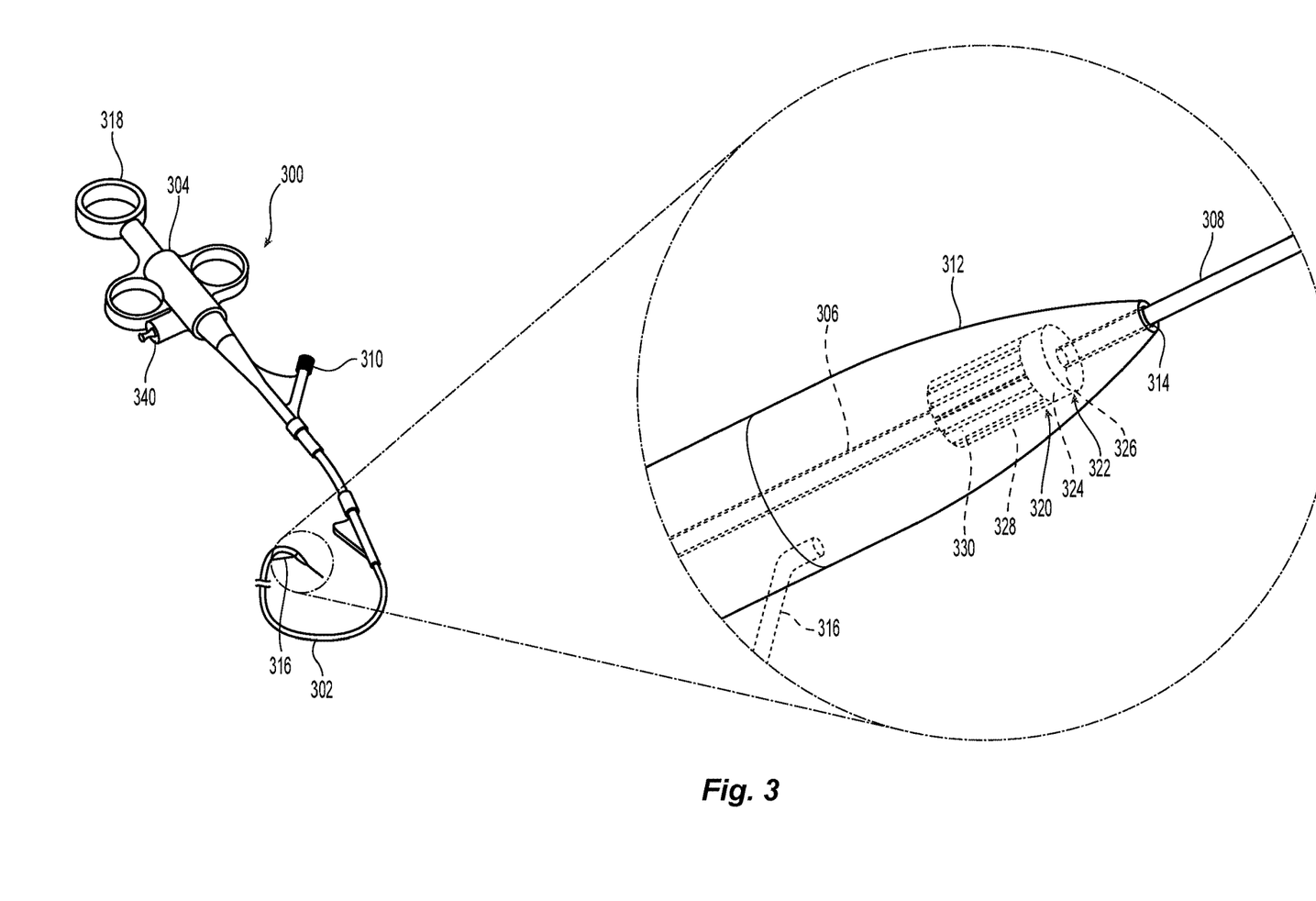
FIG. 3 is a perspective view of an exemplary cutting system, in accordance with aspects of the present disclosure.

FIG. 3 shows an exemplary cutting system 300 in accordance with aspects of the present disclosure. Cutting system 300 may include a shaft 302 and a handle 304. Shaft 302 may be an elongated flexible body that extends from a distal end of handle 304. Shaft 302 may have one or more lumens extending therethrough. For example, shaft 302 may have a working lumen 306 that allows for the passage of a guidewire 308 (or other instrument) inserted into working lumen 306 via, for example, a port 310 on handle 304. Shaft 302 may terminate with an end cap 312. End cap 312 may be rounded, tapered, stepped, enlarged, or bulbous in shape, or otherwise configured to enter a small opening in the subject's body and/or be atraumatic. Working lumen 306 may extend through end cap 312, terminating at an opening 314 through which guidewire 308 may be extended and/or retracted.

Cutting system 300 also may include a cutting wire 316. Cutting wire 316 may extend along shaft 302. In one example, a proximal portion of cutting wire 316 may extend through working lumen 306, or another lumen running parallel to working lumen 306. At a distal region of shaft 302, cutting wire 316 may exit from shaft 302 through an opening (not shown) in a wall thereof, and may extend outside of shaft 302. A distal end of cutting wire 316 may be anchored to a more distal region of shaft 302. A proximal end of cutting wire 316 may be anchored to, for example, a slidable actuator 318 of handle 304. By sliding actuator 318 proximally, the user may exert a pulling force on cutting wire 316 in the proximal direction, which may cause the distal end of shaft 302 to deflect. Cutting wire 316 may be electrically coupled to a power source via an electrical connection 340 and one or more conductors (not shown) in handle 304, such that cutting wire 316 may be energized to facilitate the cutting of tissue. In one example, cutting system 300 may be used as a sphincterotome for cutting tissue around a small opening in the subject's body. It is also contemplated that one or more steering/deflecting wires (not shown), similar to those described above with respect to endoscope system 100, may be provided in shaft 302 for steering/deflecting the distal portion of shaft 302.

Cutting system 300 may have visualization capabilities. For example, cutting system 300 may include a sonic visualization assembly 320. Sonic visualization assembly 320 may be affixed to end cap 312. Sonic visualization assembly 320 may include a forward-looking or front-end CMUT array 322 similar to front-end CMUT array 160. A distal surface of front-end CMUT array 322, which may be used to transmit and receive ultrasonic waves, may face the distal direction, and/or may extend in a plane substantially perpendicular to a central longitudinal axis of shaft 302. The field of view of front-end CMUT array 322 may cover a region immediately distal to front-end CMUT array 322, and some areas adjacent to the region. Front-end CMUT array 322 may include a plate 324. Plate 324 may be annular, having an opening 326 therein. Opening 326 may be in communication with working lumen 306. Guidewire 308 may pass through opening 326. In one example, working lumen 306 may be wider than opening 326, and as such, a radially-inner portion of front-end CMUT array 322 may protrude into working lumen 306. In another example, opening 326 may be at least as wide as working lumen 306, such that opening 326 may surround working lumen 306 without protruding into working lumen 306.

In addition to front-end CMUT array 322, or as an alternative to front-end CMUT array 322, sonic visualization assembly 320 may include a side-looking or lateral-facing CMUT array 328 similar to lateral-facing CMUT array 170. Lateral-facing CMUT array 328 may include tiles 330 in the form of polygonal plates, with transmitting and receiving surfaces of tiles 330 facing radially outwardly relative to the central longitudinal axis of shaft 302. Tiles 330 may be arranged to form a ring about shaft 302. Tiles 330 may surround working lumen 306 of shaft 302. Tiles 330 may be spaced around lumen 306 to have overlapping fields of view. It should be understood that fewer of tiles 330 may be used than shown for visualizing a smaller region of the target area.

Front-end CMUT array 322 and/or lateral-facing CMUT array 328 may be affixed to end cap 312 by adhesive bonding, heat bonding, crimping, laser welding, resistance welding, soldering, and/or any other suitable form of attachment. Front-end CMUT array 322 and/or lateral-facing CMUT array 328 may be affixed, for example, to interior and/or exterior surfaces of end cap 312. Alternatively, front-end CMUT array 322 and/or lateral-facing CMUT array 328 may be embedded within material used to form end cap 312, such that front-end CMUT array 322 and/or lateral-facing CMUT array 328 may lie between the interior and exterior surfaces of end cap 312.

Alternatively, sonic visualization assembly 320 may be similar to sonic visualization assembly 154 with front-end CMUT array 322 and/or lateral-facing CMUT array 328 arranged on a shaft (not shown) similar to shaft 156. Sonic visualization assembly 320 may be inserted through port 310 and working lumen 306 to position front-end CMUT array 322 and/or lateral-facing CMUT array 328 at end cap 312. Guidewire 308 may be inserted through a lumen of the shaft (similar to lumen 168) and maneuvered to end cap 312 for extension out of and retraction into opening 314. 2-D and 3-D visualization may be provided by sonic visualization assembly 320 in a manner similar to sonic visualization assembly 154.

Figure 4:
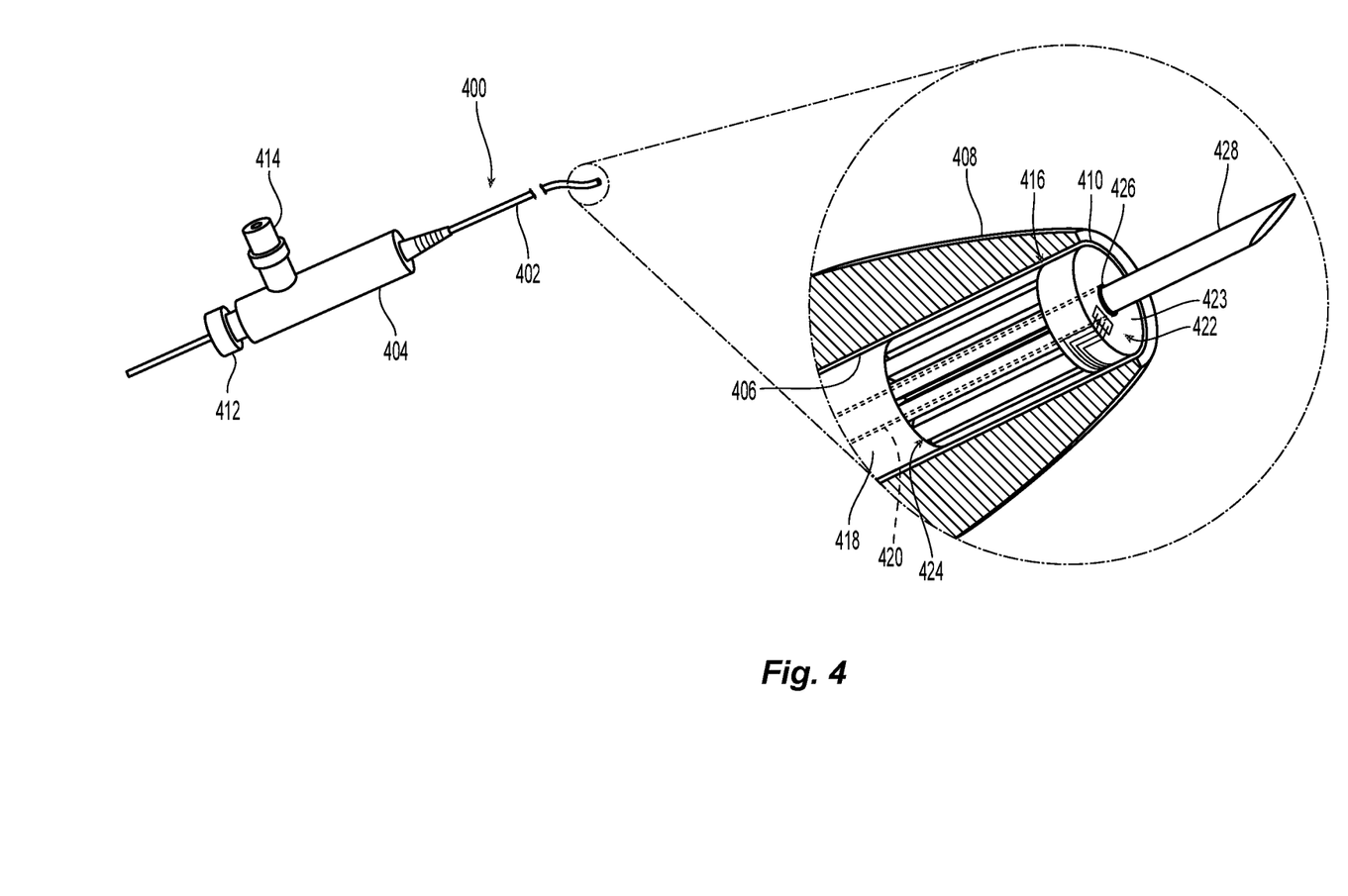
FIG. 4 is a perspective view of an exemplary injection system, including a close-up partial cross-sectional view, in accordance with aspects of the present disclosure.

FIG. 4 shows an exemplary injection and/or biopsy system 400 in accordance with aspects of the present disclosure. FIG. 4 includes a close-up view of an end portion of injection system 400. The close-up view is a partial cross-sectional view, cut away to show details of the internals of injection system 400.

Injection system 400 may include a shaft 402 and a handle 404. Shaft 402 may be an elongated flexible body that extends from a distal end of handle 404. Shaft 402 may have a working lumen 406 extending therethrough that allows for the passage of one or more instruments. Shaft 402 may terminate with an end cap 408. End cap 408 may be rounded, tapered, stepped, enlarged, or bulbous in shape, or otherwise configured to enter a small opening in the subject's body and/or be atraumatic. Working lumen 406 may extend through end cap 408, terminating at an opening 410 Working lumen 406 may be in communication with one or more of ports 412, 414 on handle 404. Injection system 400 may include, for example, an intravascular ultrasound catheter.

A sonic visualization assembly 416, similar to sonic visualization assembly 154, may be inserted into port 412 or port 414 and through working lumen 406. Sonic visualization assembly 416 may include, for example, a shaft 418 and a lumen 420 similar to shaft 156 and lumen 168, a forward-looking or front-end CMUT array 422 similar to front-end CMUT array 160, and a side-looking or lateral-facing CMUT array 424 similar to lateral-facing CMUT array 170. Front-end CMUT array 422 may be in the form of an annular plate 423 having an opening 426 therein. Opening 426 may be in communication with lumen 420. A needle 428 may be extended through lumen 420 and opening 426 to protrude distally from front-end CMUT array 422. Alternatively, a proximal end of needle 428 may be attached to the periphery of opening 426. Injection material may be introduced into needle 428 for injecting into tissue at the target area. The user may move sonic visualization assembly 416 and/or needle 428 individually, or in unison, to expose needle 428 from opening 410 to inject the material, and to cover needle 428 while needle 428 is being guided to the target area. 2-D and 3-D visualization may be provided by sonic visualization assembly 416 in a manner similar to sonic visualization assembly 154. It is also contemplated that one or more steering/deflecting wires (not shown), similar to those described above with respect to endoscope system 100 and/or cutting system 300, may be provided on or in shaft 402 for steering/deflecting the distal portion of shaft 402. While shaft 402 generally may be cylindrical, the close-up view in FIG. 4 includes a cross-sectional view of shaft 402, with a lower portion of shaft 402 cut away in the drawing to show aspects inside of shaft 402, including sonic visualization assembly 416.

One or more of endoscope system 100, endoscope system 200, cutting system 300, and injection system 400 may be used to diagnose and/or treat a target area in the subject's biliary tree. The subject's biliary tree may include a cystic duct from the subject's gall bladder, a hepatic duct from the subject's liver and a pancreatic duct from the subject's pancreas. Each of these ducts may join into the subject's common bile duct. The common bile duct may intersect with the duodenum a slight distance below the stomach. The papilla may control the size of the opening at the intersection between the bile duct and duodenum. The papilla may have to be crossed in order to reach the common bile duct to perform a biliary procedure.

In one example, a duodenoscope or other suitable outer introducer/outer sheath (not shown) may be inserted into the subject and positioned outside of the subject's common bile duct (papilla) entrance, after having traveled down the esophagus of a patient under direct visualization and arriving at, through the stomach, the duodenum at the bottom of the stomach. After positioning the distal end of the duodenoscope in the proper position, endoscope system 100, endoscope system 200, or any other suitable inner introducer/inner sheath may be advanced through and out of the duodenoscope for cannulating the papilla. After cannulating the papilla, endoscope system 100 or endoscope system 200 may be advanced further into the common bile duct. Sonic visualization assembly 154, sonic visualization assembly 206, cutting system 300, and/or injection system 400 may be at least partially contained within endoscope system 100 or endoscope system 200, and may be used for visualization to facilitate cannulating of the papilla and/or insertion into the common bile duct.

In one example, once endoscope system 100 or endoscope system 200 is in place, sonic visualization assembly 154, sonic visualization assembly 206, cutting system 300, and/or injection system 400 may be advanced to the target area by passing through working lumen 108 or a working lumen 216. A front-end CMUT array (e.g., front-end CMUT array 160, 218, 322, or 424) and/or lateral-facing CMUT array (e.g., lateral-facing CMUT array 170, 208, 328, or 424) may provide the user with 2-D and/or 3-D visualizations of tissue in the bile duct for diagnosis and/or treatment. Cutting system 300 may be used to cut tissue of the bile duct, for example, in an endoscopic biliary sphincterotomy procedure. Injection system 400 may be used to inject material into the bile duct or its tissue, or to remove (e.g., core) bile duct tissue, using needle 428.

It should be understood, however, that similar steps may be performed to diagnose and/or treat other areas of the subject's body. For example, endoscope system 100 or endoscope system 200 may be introduced into the subject's lungs. There, sonic visualization assembly 154, sonic visualization assembly 206, cutting system 300, and/or injection system 400 may provide the user with 2-D and/or 3-D visualizations of tissue in the lungs for diagnosis and/or treatment. Cutting system 300 may be used to cut lung tissue. Injection system 400 may be used to inject material into the lung or its tissue, or to remove (e.g., core) lung tissue, using needle 428.

It will be apparent to those skilled in the art that various modifications and variations can be made in the disclosed apparatuses and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A system for visualizing a target area, comprising:
    an elongate shaft, including:
        a distal portion,
        a lumen that extends longitudinally through the distal portion, and
        a first opening at a distal end of the distal portion, wherein the first opening is in communication with the lumen; and
    a visualization assembly housed within the distal portion of the elongate shaft, wherein the visualization assembly includes a transducer array having a field of view in which the transducer array transceives sound waves, and the field of view of the transducer array covers at least part of the distal portion of the elongate shaft and the target area to facilitate visualization of the part of the distal portion of the elongate shaft and the target area at a same time, wherein the transducer array includes a plate, and a second opening extends through the plate,
    wherein a portion of the distal end of the distal portion of the elongate shaft includes a taper such that at least a portion of a radially outermost surface of the transducer array is exposed from the elongate shaft by the taper.

2. The system of claim 1, wherein the transducer array surrounds at least a portion of the second opening.

3. The system of claim 1, wherein the transducer array includes at least one ultrasonic transducer.

4. The system of claim 3, wherein the ultrasonic transducer includes a capacitive micromachined ultrasonic transducer.

5. The system of claim 1, wherein the elongate shaft includes a third opening at the distal end of the distal portion, and the system further includes an optical visualization assembly received in the third opening.

6. The system of claim 1, wherein the elongate shaft has a distalmost end, and the transducer array includes at least one transducer configured to transmit sound waves toward a region distal to the distalmost end, and to receive sound waves from the region.

7. The system of claim 1, wherein the transducer array includes at least one transducer on a side of the visualization assembly.

8. The system of claim 7, wherein the at least one transducer includes a plurality of plates, each of the plates has a plurality of transducers thereon, and the plates are arranged in a ring formation.

9. The system of claim 1, wherein the transducer array includes at least one transducer configured to transmit sound waves toward a region lateral to the distal portion of the elongate shaft, and receive sound waves from the region.

10. The system of claim 1, further including a control member coupled to the distal portion of the elongate shaft to exert a deflecting force on the distal portion, such that the visualization assembly deflects with the distal portion.

11. The system of claim 1, further comprising a second elongate shaft disposed within the lumen and configured to move relative to the elongate shaft, wherein the plate is attached to a distal end of the second elongate shaft.

12. A system for visualizing a target area, comprising:
    an introducer, including:
        a first elongate shaft, and
        a plurality of lumens in the first elongate shaft, wherein the plurality of lumens includes a first lumen that extends longitudinally through the first elongate shaft; and
    a visualization assembly slidably received by the introducer, the visualization assembly including:
        a second elongate shaft, and
        a transducer array at a distal portion of the second elongate shaft, wherein the transducer array is configured to transceive sound waves for visualization of the target area, and to slide proximally and/or distally relative to the first elongate shaft within the first lumen, and wherein the transducer array includes a plate having an opening extending through the plate, wherein a portion of a distal end of the first elongate shaft includes a taper such that at least a portion of a radially outermost surface of the transducer array is exposed from the first elongate shaft by the taper.

13. The system of claim 12, wherein the introducer further includes an optical visualization assembly, and the optical visualization assembly includes an imaging device at a distal end of the introducer.

14. The system of claim 12, wherein the transducer array is extendable distally beyond the distal end of the first elongate shaft.

15. The system of claim 12, wherein the transducer array includes a capacitive micromachined ultrasonic transducer array.

* * * * *